United States Patent [19]
Hamilton

[11] Patent Number: 5,444,265
[45] Date of Patent: Aug. 22, 1995

[54] METHOD AND APPARATUS FOR DETECTING DEFECTIVE SEMICONDUCTOR WAFERS DURING FABRICATION THEREOF

[75] Inventor: Jeffrey L. Hamilton, Livermore, Calif.

[73] Assignee: LSI Logic Corporation, Milpitas, Calif.

[21] Appl. No.: 21,426

[22] Filed: Feb. 23, 1993

[51] Int. Cl.6 .............................................. G01N 21/88
[52] U.S. Cl. ........................ 250/559.42; 250/559.29; 356/237
[58] Field of Search ............... 250/561, 562, 571, 572; 356/237, 429, 430; 437/7, 8; 29/25.01

[56] References Cited

U.S. PATENT DOCUMENTS

| | | | |
|---|---|---|---|
| 3,474,254 | 10/1969 | Piepenbrink et al. | 356/430 |
| 3,922,093 | 11/1975 | Dandliker et al. | 250/571 |
| 3,931,525 | 1/1976 | Clarke | 250/572 |
| 4,029,420 | 6/1977 | Simms | 356/444 |
| 4,092,068 | 5/1978 | Lucas | 250/572 |
| 4,131,803 | 12/1978 | Takematsu et al. | 250/572 |
| 4,184,082 | 1/1980 | Peoples | 250/572 |
| 4,389,575 | 6/1983 | Cole | 356/430 |
| 4,740,708 | 4/1988 | Batchelder | 356/237 |
| 4,768,878 | 9/1988 | Heine et al. | 356/237 |
| 4,988,875 | 1/1991 | Ortiz et al. | 250/562 |

*Primary Examiner*—Stephone B. Allen

[57] ABSTRACT

An apparatus and method for detecting burnt resist or mask on the surface of a semiconductor integrated circuit wafer during fabrication thereof. A light source and light sensor are utilized to identify the flat matte surface finish of burnt resist or mask and shut down the fabrication process before a large number of semiconductor wafers are ruined. The burnt resist or mask is detected by the lack of reflected light from the surface of the wafer compared with the light reflected from the surface of a known good resist coated wafer.

16 Claims, 4 Drawing Sheets

METHOD AND APPARATUS FOR DETECTING DEFECTIVE SEMICONDUCTOR WAFERS DURING FABRICATION THEREOF

BACKGROUND OF THE INVENTION

1. Field of the Invention

This invention relates generally to detecting defective semiconductor integrated circuit wafers during fabrication thereof, and in particular, to an apparatus and method that detects burnt material on the surface of the integrated circuit wafer by the lack of light reflectance therefrom.

2. Description of the Related Technology

The semiconductor integrated circuit has revolutionized the field of electronics by becoming a basic building block in electronic products. The integrated circuit has created many new products and services in the consumer, industrial and military markets. As new products were introduced, the more popular ones created a great demand for the integrated circuits used to build these products.

This resulted in a new industry devoted to manufacturing semiconductor integrated circuits in quantity and at a price that was acceptable in the various electronic markets. In order to keep the price of integrated circuits as low as possible, assembly line, automation and large quantity manufacturing techniques were required.

Semiconductor integrated circuits are manufactured or fabricated by creating electronic circuits such as transistors, diodes, resistors and capacitors on a silicon substrate. This silicon substrate is a wafer cut from a pure silicon crystal grown specifically for use in manufacturing integrated circuits. The silicon wafer is normally cut to resemble a thin circular disk of about 4 to 6 inches in diameter. The wafer is smoothly polished to a mirror-like surface and then the fabrication process of creating the electronic circuits begins.

The fabrication process begins by selectively doping the surface area of the silicon wafer with impurities to create negative channel (N—channel) or positive channel (P—channel) regions to create transistors and diodes. Interconnections, resistors and capacitors are fabricated by selectively plating metal onto the surface of the silicon wafer. Insulation between layers of electronic components is fabricated by selectively coating the areas of the wafer requiring insulation.

An integrated circuit wafer is comprised of a plurality of integrated circuit chips that ultimately are fabricated into integrated circuit packages for use in building electronic products. Thus, during integrated circuit chip fabrication, a plurality of duplicate fabrication operations are performed on the silicon wafer.

These fabrication operations consist of applying photo resist to the surface of the wafer and selectively etching parts of the silicon wafer to produce the required electronic circuits. Integrated circuit fabrication involves a plurality of steps that layer specific patterns of protective coatings onto the surface of the wafer, then doping, etching or depositing metal at the unprotected areas of the wafer. After the coating, doping, etching and depositing of metal steps are completed, The wafer is cut into individual integrated circuit chips for packaging into finished integrated circuit products.

A necessary step in the aforementioned fabrication process is depositing and curing the protective coatings or "resist" onto the wafer surface. The resist is cured with heat, and sometimes, if the process parameters are not adjusted correctly or the process equipment malfunctions, excessive heat will discolor or "burn" the resist surface. In similar fashion, coatings of organic material such as, for example, polymers including polyimide and epoxy may be used on the surface of the integrated circuit wafer die. Burnt resist or mask is not desirable because it introduces contaminates into and causes other problems in the integrated circuit fabrication process.

Detection of burnt resist or mask was not made until wafer etch inspection, resulting in the loss of many wafers. The number of wafers lost depends on the fabrication lag time from resist cure to etch inspection. With highly automated integrated circuit fabrication assembly lines, the number of undetected burnt resist or mask wafers can be enormous. In addition, as integrated circuits become more complex and expensive, the cost in spoilage becomes a significant part of the overall manufacturing costs. This is especially true when small quantity production run, or custom order application-specific integrated circuits (ASIC) are being produced.

What is needed in semiconductor integrated circuit manufacturing is more timely detection of burnt resist or mask during the wafer fabrication process. Preferably some form of automatic detection of burnt resist would be desirable so that the wafer manufacturing process could quickly be shut down while corrective adjustments to the process are made.

SUMMARY OF THE INVENTION

In contrast to prior methods of detecting burnt resist or mask during later inspection stages of the semiconductor manufacturing process, the present invention provides a method and apparatus for quickly and automatically detecting burnt resist or mask before a large number of wafers are irreparably damaged. The present invention utilizes one or more sensors to detect the amount of light reflected from the surface of a semiconductor integrated circuit wafer.

Burnt resist or mask typically has a flat matte surface finish that does not substantially reflect light. Properly cured resist is clear and allows light to be substantially reflected off the reflective surface of the wafer. By calibrating the light sensors with a wafer having a coating of properly cured resist, and with a wafer having burnt resist or mask, good and bad detection levels from the light sensor may be established for alarm and shutdown purposes. Thus, the sensors may be used to identify the flat matte surface finish of burnt resist or mask and to shut down the fabrication process before a large number of semiconductor wafers are ruined.

The embodiment of the present invention utilizes a plurality of light beam sensors that "see" the presence of wafers having the desired resist or mask coating by the amount of light reflected therefrom, and do not "see" the presence of wafers having burnt resist. A second sensor detects the presence of a wafer, whether having burnt resist or not. The combination of the light beam sensor and the presence sensor combines to indicate a "good" wafer suitable for further processing. When a wafer is detected by the presence sensor, but not the light beam sensor, then the wafer fabrication process is halted and corrective adjustments are made thereto.

Fiber optics may be utilized to reduce the number of light beam sensors or to allow the sensors to be remotely mounted. Light may be sent to the surface of selected parts of the wafer by the fiber optic light transmitters, and a single sensor may be used to determine the light reflected off the surface of the selected part of the wafer. If the selected part of the wafer has burnt resist, then substantially no light will be reflected therefrom. The fiber optics bundle may be utilized to cover a finer area of the wafer than could otherwise be done by shining a single light beam directly onto the surface of the wafer and then detecting the light reflected therefrom with a sensor.

An object of the present invention is to identify the flat matte finish of burnt resist or mask on a semiconductor integrated circuit wafer during fabrication thereof.

Another object of the present invention is to provide for alarm and shutdown of the wafer fabrication process when the presence of burnt resist or mask is identified.

A further object of the present invention is to determine the presence of a semiconductor integrated circuit wafer having burnt resist or mask thereon during fabrication thereof.

A feature of the present invention is utilizing an integrated light beam and sensor for detecting light reflected off the surface of a semiconductor wafer.

Another feature of the present invention is utilizing a plurality of light beams and sensors for detecting light reflected off selected areas of the surface of a semiconductor wafer.

Still a further feature of the present invention is utilizing fiber optics to transmit the light to selected areas of the surface of a semiconductor wafer, and sensing the reflected light therefrom with a light detection sensor.

An advantage of the present invention is early detection of burnt resist or mask before a large quantity of semiconductor integrated circuit wafers are ruined.

Another advantage of the present invention is automatic alarm and shutdown of a wafer fabrication process upon detection of burnt resist or mask.

Other and further objects, features and advantages will be apparent from the following description of a presently preferred embodiment of the invention, given for the purpose of disclosure and taken in conjunction with the accompanying drawings.

DETAILED DESCRIPTION OF THE PREFERRED EMBODIMENT

Figure 1:
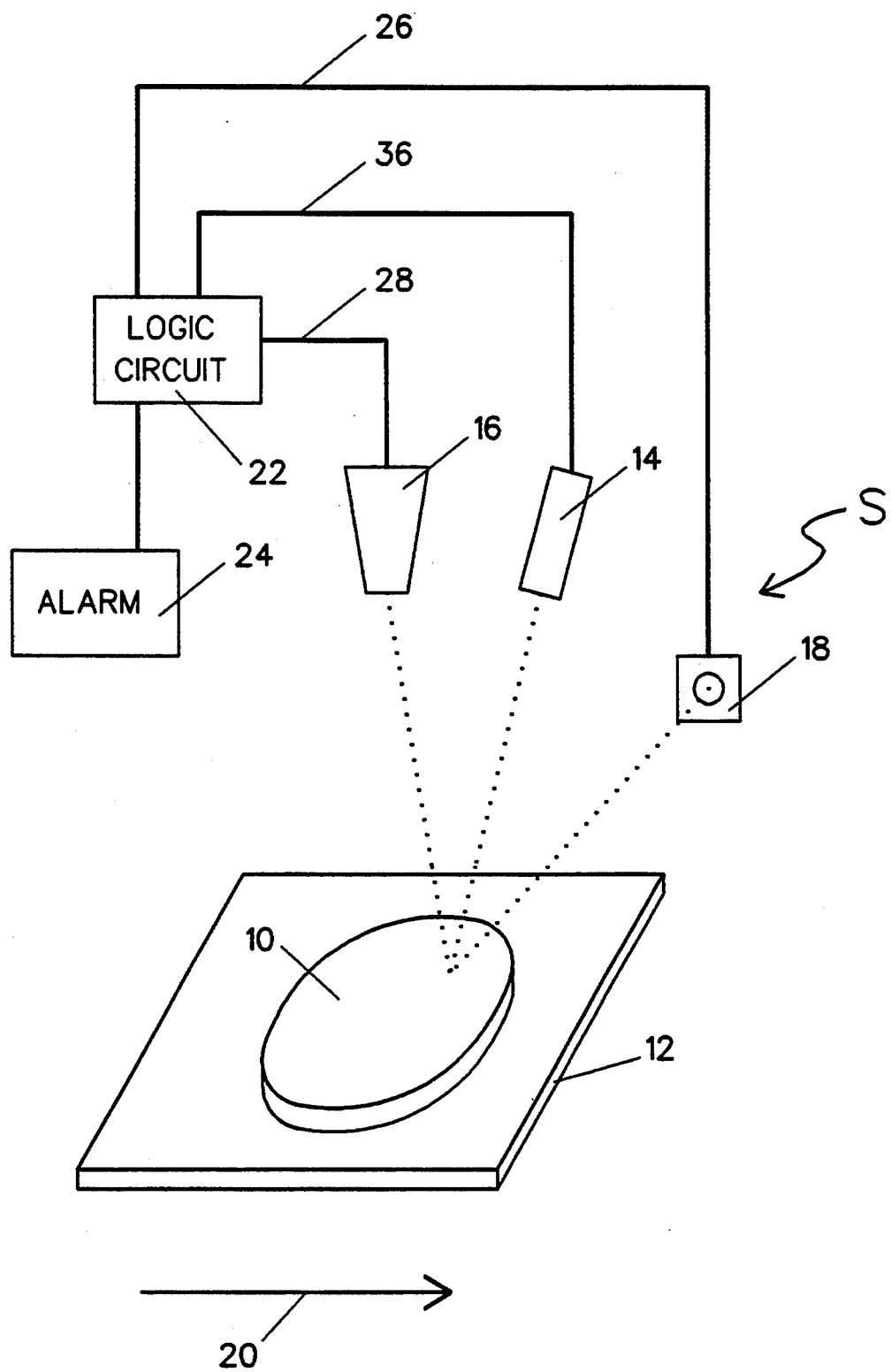
FIG. 1 is a schematic perspective view of the embodiment of the present invention.

Referring now to the drawings, the details of the preferred embodiment are schematically illustrated. In the drawings, the letter S designates generally an apparatus for determining when the resist on an integrated circuit is burnt. Like elements are numbered the same, and similar elements are represented by the same number and a different lower case letter thereafter.

The burnt resist or mask detector system S is illustrated in perspective view schematically in FIG. 1. The burnt resist detector S comprises a light source 14, a light sensor 16, a wafer presence sensor 18 and a logic circuit 22 for determining when a wafer 10 is present but there is substantially no light reflected from the surface of the wafer 10. The wafer 10 travels on wafer carrier 12 in direction 20 during fabrication of the integrated circuit wafer.

The light source 14 illuminates the surface of the wafer 10 and any light reflected therefrom is detected by the light sensor 16. The wafer moves generally in direction 20 on carrier 12. Presence sensor 18 determines when the wafer 10 is in the illumination area of light source 14.

Logic circuit 22 receives a wafer presence signal 26 from sensor 18 and a detected light sensor signal 28 from light sensor 16. Signal 28 is proportional to the detected light reflected from the surface of the wafer 10. There will be substantially no reflected light detected by sensor 16 if the resist or mask is burnt on the surface of wafer 10. Good resist is normally clear and does not restrict light from being reflected from the surface of the wafer 10. Mask may be clear or of a light reflective color. Therefore, the signal 28 will be high when the resist is clear (mask is clear or light reflective) as is expected in normal fabrication, but will be low if the resist or mask is burnt.

The logic circuit 22 determines that when the wafer presence signal 26 indicates a wafer 10 is present, the reflected light sensor signal 28 should be high also. If the reflected light sensor signal 28 is not high, the logic circuit 22 causes an alarm 24 to sound. Upon the sounding of alarm 24, the fabrication process can be shut down and the problem causing the burnt resist corrected. The logic circuit 22 may also be used to automatically shut down the integrated circuit wafer fabrication process.

Figure 2:
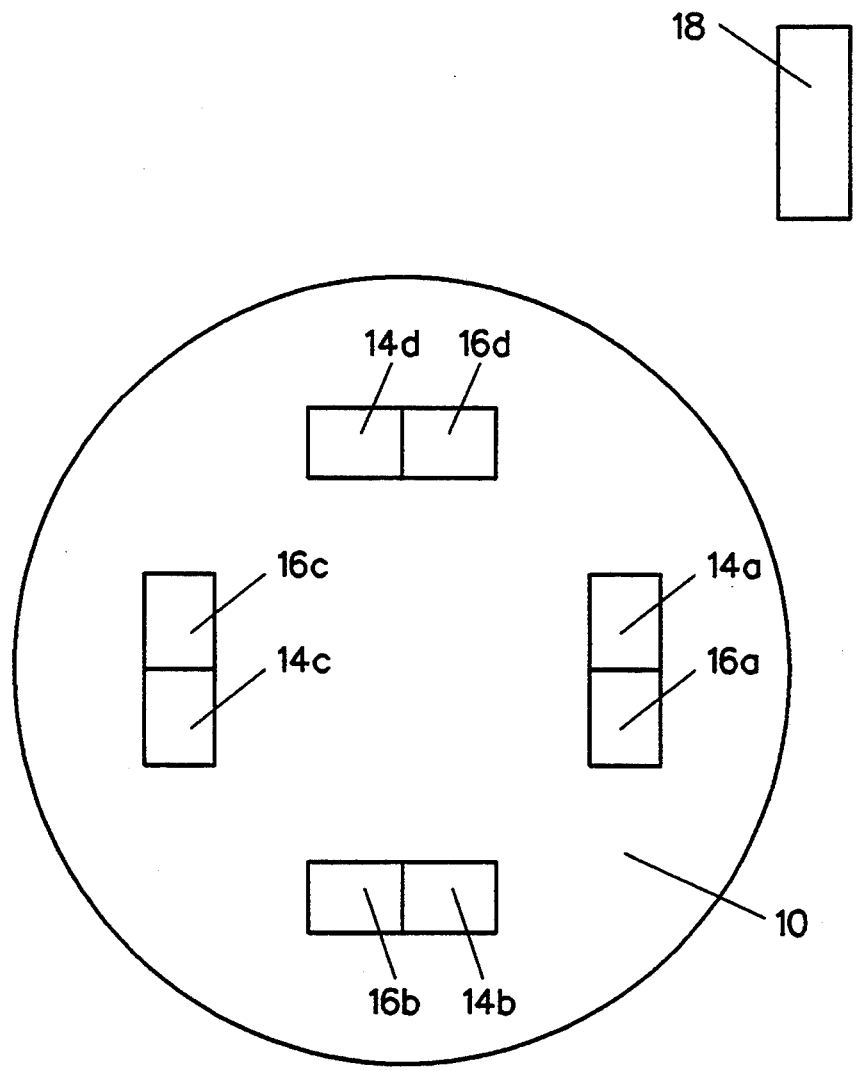
FIG. 2 is a schematic plan view of FIG. 1 with the addition of a plurality of light beam/sensors.

Referring now to FIG. 2, a multiple light source light sensor embodiment of the present invention is illustrated schematically in plan view. Light sources 14a, 14b, 14c and 14d each illuminate a quarter of the surface of wafer 10. Light detector sensors 16a, 16b, 16c and 16d detect the reflected light from each respective quarter surface of the wafer 10. Sensor 18 detects the presence of the wafer 10.

The light sources 14a, 14b, 14c and 14d may simultaneously illuminate the surface of wafer 10 or the light sources 14a, 14b, 14c and 14d may sequentially illuminate each respective quarter surface of wafer 10. The light detector sensors 16a, 16b, 16c and 16d are adjusted to detect their respective quarter surface of the wafer 10.

Figure 3:
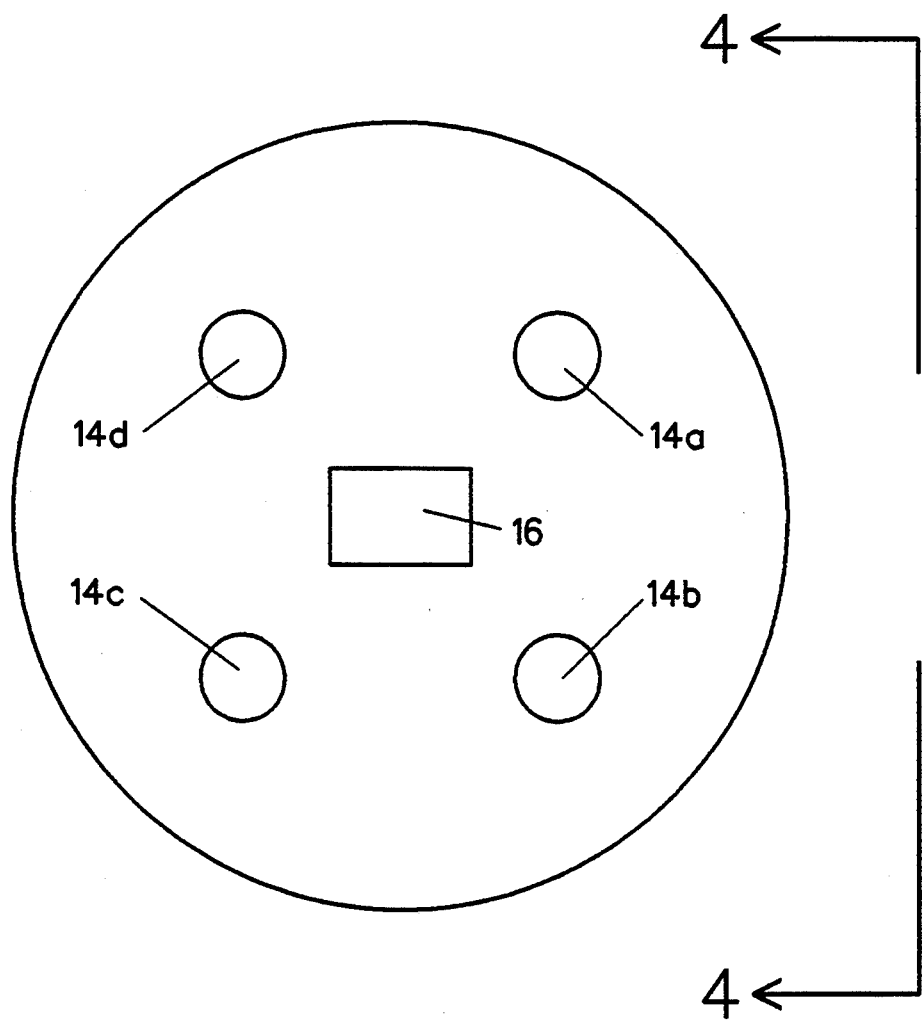
FIG. 3 is a schematic plan view of another embodiment having multiple light sources and one light sensor.
Figure 4:
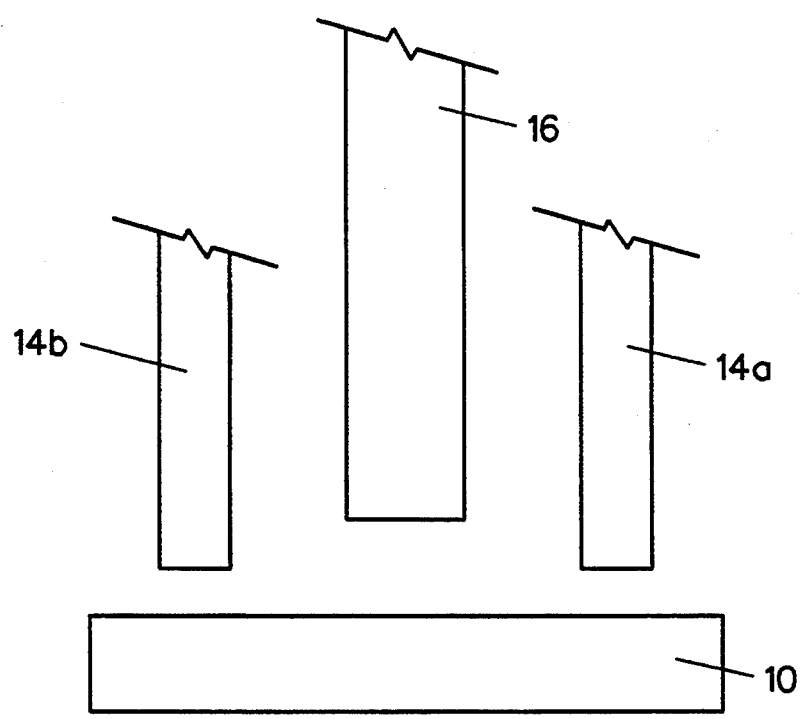
FIG. 4 is a schematic elevational sectional view of FIG. 3.

Referring now to FIGS. 3 and 4, a multiple light source and single light detection sensor is illustrated in schematic plan and elevational views, respectively. The light sources 14a, 14b, 14c and 14d illuminate their respective quarter surfaces of the wafer 10. These light sources may use fiber optics to conduct the light therethrough. A single light detector sensor 16 sequentially detects light reflected from each respective quarter surface of the wafer 10.

A plurality of burnt resist or mask detectors S may be utilized for determining the resist condition of a plurality of wafers 10 (not illustrated).

The system and method of the present invention, therefore, is well adapted to carry out the objects and attain the ends and advantages mentioned, as well as others inherent therein. While a presently preferred embodiment of the invention has been given for purposes of disclosure, numerous changes in the details of construction, interconnection and arrangement of parts will readily suggest themselves to those skilled in the art and which are encompassed within the spirit of the invention and the scope of the appended claims.

What is claimed is:

1. A method for determining when a coating on the surface of a semiconductor integrated circuit wafer is burnt during fabrication thereof, comprising the steps of:

detecting the presence of the semiconductor integrated circuit wafer;

illuminating the coated surface of the semiconductor integrated circuit wafer with light;

measuring the light reflected off the coated semiconductor integrated circuit wafer;

determining whether the coating is burnt by the amount of light reflected from the surface of the coated semiconductor integrated circuit wafer; and alarming when burnt coating is so determined.

2. The method of claim 1, further comprising the step of stopping the semiconductor integrated circuit wafer fabrication process when burnt coating is determined.

3. The method of claim 1, wherein the step of measuring the light reflected off the surface of the coated semiconductor integrated circuit wafer includes measuring light reflected off of a resist coating.

4. The method of claim 1, wherein the step of measuring the light reflected off the surface of the coated semiconductor integrated circuit wafer includes measuring light reflected off of a polymer mask coating.

5. The method of claim 1, wherein the step of measuring the light reflected off the surface of the coated semiconductor integrated circuit wafer includes measuring light reflected off of a polyimide mask coating.

6. The method of claim 1, wherein the step of measuring the light reflected off the surface of the coated semiconductor integrated circuit wafer includes measuring light reflected off of an epoxy mask coating.

7. An apparatus for determining when a coating on the surface of a semiconductor integrated circuit wafer is burnt during fabrication thereof, comprising:

a light source, said light source illuminating the surface of the semiconductor integrated circuit wafer;

a light sensor, said light sensor detecting reflected light from the surface of the wafer, wherein burnt coating will substantially prevent reflection of light from the surface of the wafer;

means to detect the presence of the wafer; and logic means for alarming when a wafer is present and there is substantially no reflected light from the surface of the wafer, said logic means connected to and receiving signals from said light sensor and wafer presence detection means.

8. The apparatus of claim 7, wherein said light source is a plurality of light sources sequentially enabled to illuminate selected areas of the wafer.

9. The apparatus of claim 7, wherein said light sensor is a plurality of light sensors, each light sensor detecting reflected light from a selected area of the wafer.

10. The apparatus of claim 7, wherein said presence detection means is a proximity switch.

11. The apparatus of claim 7, wherein said presence detection means is a lever actuated switch.

12. The apparatus of claim 7, wherein said presence detection means is a light source and light sensor that detects the presence of the wafer when the wafer passes between the light source and the light sensor, and interrupts the light therebetween.

13. The apparatus of claim 7, wherein said logic means comprises:

a selectably adjustable analog relay having a low set point representative of substantially no light reflected from the surface of the wafer, indicating burnt coating, and a high set point representative of light reflected from the surface of the wafer, indicating normal coating, said analog relay having an output logic signal representative of the high set point; and a logic circuit having an output signal when the presence of a wafer is detected and there is no logic signal from said analog relay indicating a high set point, said logic circuit output signal adapted to actuate an alarm.

14. The apparatus of claim 7, wherein the coating is resist.

15. The apparatus of claim 7, wherein the coating is an organic material mask.

16. The apparatus of claim 15, wherein the organic material mask comprises polyimides and epoxies.

* * * * *